US007282325B2

(12) United States Patent
Hebebrand et al.

(10) Patent No.: US 7,282,325 B2
(45) Date of Patent: *Oct. 16, 2007

(54) METHOD OF PREPARING PHARMACEUTICAL COMPOSITIONS

(75) Inventors: Johannes Hebebrand, Marburg/Lahn (DE); Jochen Antel, Bad Muender (DE); Ulf Preuschoff, Lehrte/Ahlten (DE); Samuel David, Hannover (DE); Holger Sann, Hannover (DE); Michael Weske, Burgdorf (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 18 days.

This patent is subject to a terminal disclaimer.

(21) Appl. No.: 10/785,043

(22) Filed: Feb. 25, 2004

(65) Prior Publication Data

US 2004/0167214 A1     Aug. 26, 2004

Related U.S. Application Data

(62) Division of application No. 09/907,440, filed on Jul. 18, 2001, now Pat. No. 6,946,243.

(60) Provisional application No. 60/219,672, filed on Jul. 21, 2000.

(30) Foreign Application Priority Data

Jul. 20, 2000   (DE)   ................. 100 35 227

(51) Int. Cl.
    *C12Q 1/00*   (2006.01)
(52) U.S. Cl. .............. 435/4; 435/18; 435/69.2
(58) Field of Classification Search ...... None
    See application file for complete search history.

(56) References Cited

U.S. PATENT DOCUMENTS

| 5,597,797 | A  | * | 1/1997 | Clark ........................... 514/12 |
| 6,288,095 | B1 | * | 9/2001 | Hindley et al. ............. 514/367 |
| 6,946,243 | B2 | * | 9/2005 | Hebebrand et al. ............ 435/4 |
| 2003/0100594 | A1 | * | 5/2003 | Masferrer et al. .......... 514/406 |

FOREIGN PATENT DOCUMENTS

| EP | 0138441 | | 4/1985 |
| WO | WO-94/09813 A1 | | 5/1994 |
| WO | WO 98/00130 | * | 1/1998 |
| WO | WO9800130 | | 1/1998 |

OTHER PUBLICATIONS

Dulloo A. et al. Screening of Drugs for Thermogenic Anti-Obesity Properties: Antidepressants. Ann Nutr Metab 31(2)69-80, 1987.*
Hazen, S. Differentiation Dependent Expression of CA V and the Role of Carbonic Anydrase Isozymes in Pyruvate Carboxylation in Adipocytes. FASEB J 1006, 10(4)481-490.*
Karl M. Wilbur, "Electrometric and Colorimetric Determination of Carbonic Anhydrase" Journal of Biological Chemistry vol. 176, 1948.
Claudia T. Supuran, "Carbonic anhydrase inhibitors and their therapeutic potential" Ashley Publications Ltd., pp. 1354-3776, 2000.
MK Hellerstein, "De novo lipogenesis in humans: metabolic and regulatory aspects" European Journal of Clinical Nutrition, 1993.
Bruce E. Maryanoff, "Structure-Activity Studies on Anticonvulsant Sugar Sulfamates Related to Topiramate. Enhance Potency with Cyclic Sulfate Derivatives" J. Med. Chemistry, vol. 41, pp. 1315-1343, 1998.
Susanna J. Dodgson, "Topiramate as an Inhibitor of Carbonic Anhydrase Isoenzymes" Epilepsia, vol. 41, 2000.
Y. Pocker, J.T. Stone, "The Catalytic Versatility of Erythrocyte Carbonic Anhydrase. The Enzyme-Catalyzed Hydrolysis of p-Nitrophenyl Acetate" Journal of the American Chemistry Society, 87:23, 1965.
Robert W. Heck, "Catalytic Properties of Mouse Carbonic Anhydrase V*" The Journal of Biological Chemistry, vol. 269, No. 40, 1994.
Claudiu T. Supuran, et al., "Carbonic anhydrase inhibitors and their therapeutic potential" Expert Opinion on Therapeutic Patents, 2000.
M. K. Hellerstein, et al., "De novo lipogenesis in humans: metabolic and regulatory aspects" European Journal of Cliinical Nutrition, 1999.
Gautam Sanyal, "Thermodynamics of Carbonic Amhydrase Catalysis" The Journal of Biological Chemistry, vol. 256, No. 2, 1981.
James E. P. Toman, "Properties of Maximal Seizures, and their Alteration by Anticonvulsant Drugs and other Agents" University of Utah School of Medicine, 1946.

(Continued)

*Primary Examiner*—Ralph Gitomer
(74) *Attorney, Agent, or Firm*—Crowell & Moring LLP

(57) ABSTRACT

A method for the discovery of compounds suitable for the treatment and/or prophylaxis of obesity, in which the ability of the test compounds to inhibit de novo lipogenesis in mammals and/or man is determined. The use of compounds which are capable of inhibiting de novo lipogenesis in mammals, and which are substantially free of effects directed towards the CNS, for the preparation of pharmaceutical compositions for the treatment and/or prophylaxis of obesity, as well as for the treatment and/or inhibition of obesity, are also described.

2 Claims, No Drawings

OTHER PUBLICATIONS

Y. Pocker, "The Catalytic Versatility of Erythrocyte Carbonic Anhydrase III. Kinetic Studies of the Enzyme-Catalyzed Hydrolysis of ρ-Nitrophenyl Actate" Biochemistry, vol. 6, No. 3, 1967.

Claudia T. Supuran, "Carbonic anhydrase inhibitors-Part 53. Synthesis of substituted-pyridinium derivatives of aromatic sulfonamides: The first non-polymeric membrane-impermeable inhibitors with selectivity for isozyme IV" Eur. J. Med. Chemistry, vol. 33, 1998.

Graham Chen, "Evaluation of Five Methods for Testing Anticonvulsant Activities" Department of Pharmacology, Parks, Davis & Co., 1954.

Andrea Scozzafava, "Carbonic Anhydrase Inhibitors: Synthesis of Water-Soluble, Aminoacyl/Dipeptidyl Sulfonamides Possessing Long-Lasting Intraocular Pressure-Lowering Properties via the Topical Route" J. Med. Chemistry, vol. 42, 1992.

Raja G. Khalifah, "The Carbon Dioxide Hydration Activity of Carbonic Anhydrase" The Journal of Biological Chemistry, vol. 246, No. 8, 1971.

Stacy A. Hazen, "Differentiation-dependent expression of CA V and the role of carbonic anhydrase isozymes in pyruvate carboxylation in adipocytes" The FASEB Journal, 1995.

Bruce E. Maryanoff, "Anticonvulsant O-Alkyl Sulfamates. 2,3:4,5-Bis-O- (1-methylethylidene) -B-D-fructopyranose Sulfamate and Related Compounds" American Chemistry Society, 1987.

* cited by examiner

METHOD OF PREPARING PHARMACEUTICAL COMPOSITIONS

CROSS-REFERENCE TO RELATED APPLICATIONS

This application is a division of U.S. application Ser. No. 09/907,440, filed Jul. 18, 2001, now U.S. Pat. No. 6,946,243, issued Sep. 20, 2005, which is an application claiming the benefit under 35 U.S.C. §119(e) of U.S. provisional application Ser. No. 60/219,672, filed Jul. 21, 2000, which claims the priority to German patent Application No. 100 35 227.8, filed Jul. 20, 2000, the entire disclosures of which are hereby incorporated by reference in their entirety.

BACKGROUND OF THE INVENTION

The present invention relates to a method of identifying compounds suitable for the treatment and/or prophylaxis of obesity. The invention further relates to the use of compounds which are capable of inhibiting de novo lipogenesis in mammals, and which are substantially free of effects directed towards the central nervous system (=CNS), for the preparation of drugs for the treatment and/or prophylaxis of obesity.

Today, especially in the developed industrial nations, obesity is an increasingly serious problem for the health of the population, being caused predominantly by unbalanced and excessively high-fat nutrition. The increase in the percentage of overweight people in the population is being accompanied by an increase in the consequences of obesity, which range from personal discontentment to cardiovascular disease or certain forms of diabetes. There are therefore already a number of therapeutic procedures aimed at the treatment or prophylaxis of obesity. One example which may be mentioned is lipase-inhibitory compounds, which reduce lipolysis in the intestinal tract and thereby cut down the energy yield from the food intake. Thus, in this therapeutic procedure, at least part of the alimentary fats is excreted undecomposed. It is however desirable to have other novel therapeutic procedures for the treatment and/or prophylaxis of obesity which can complement the previously known forms of therapy.

SUMMARY OF THE INVENTION

It has now been found, surprisingly, that compounds which are capable of inhibiting de novo lipogenesis in mammals, especially man, are advantageously suitable for the effective treatment and/or prophylaxis of obesity. Particularly good results are achieved by administering the above-mentioned compounds over prolonged periods, for example for periods of several weeks.

The invention thus relates to a method of discovering compounds suitable for the treatment and/or prophylaxis of obesity, in which those compounds are selected which are capable of inhibiting de novo lipogenesis in mammals, especially man. Furthermore, the invention also relates to the use of compounds which are capable of inhibiting de novo lipogenesis in mammals, and which are in particular substantially free of effects directed towards the CNS, such as anticonvulsant effects, for the preparation of pharmaceutical compositions for the treatment and/or prophylaxis of obesity, as well as to a method of treating or inhibiting obesity.

De novo lipogenesis (abbreviated hereafter to DNL) is understood as meaning the synthesis of endogenous fatty acids from carbohydrates in the mammalian organism. This synthetic reaction takes place in the cytosol of body cells and is based on the so-called citric acid cycle or Krebs-Martius cycle. In this cycle, in an endogenous biochemical reaction, citrate is ultimately synthesized from the two components pyruvate, which originates from carbohydrates, and bicarbonate via different intermediates—including maleate, fumarate and α-ketoglutarate. If citrate is synthesized in excess, it can be converted via the intermediate acetyl-coenzyme A to free fatty acids (=lipidic subsequent products), which form fats and can then be stored in fat cells (=adipocytes). The excessive storage of fats formed from fatty acids in body cells can quite generally lead to obesity. A variety of enzymes participate in the citric acid cycle. The turnover of the citrate cycle depends substantially on the amount of bicarbonate available. The amount of bicarbonate available in turn depends on the rate at which it can be formed from carbon dioxide. This bicarbonate-yielding equilibrium reaction is catalyzed by so-called carboanhydrases. Of the known carboanhydrases and isozymes thereof, predominantly carboanhydrase isozymes of subtypes II (=CA II) and V (=CA V) participate, in mammals, in the catalysis of reactions which provide bicarbonate for the citric acid cycle. Carboanhydrases of subtype V, which are present in the mitochondria, have a particular role to play. The citric acid cycle also takes place in the mitochondria.

There are various conceivable possibilities for inhibiting DNL in mammalian cells, all of which aim to reduce the turnover of the citric acid cycle. This makes it possible to cut down the concentration of citrate produced in excess, which is available for the synthesis of fatty acids. According to the present invention, DNL can preferably be inhibited by inhibiting the carboanhydrases which catalyze the reactions yielding bicarbonate for the citric acid cycle. For the purpose of the invention, it is possible to inhibit preferably carboanhydrases of subtypes II and/or V and particularly preferably CA V.

Compounds which are capable of inhibiting carboanhydrases non-specifically (=non-specific or conventional CA inhibitors) are known per se and have been used for a relatively long time in various therapeutic fields, mainly as diuretics or in ophthalmology. A survey of fields of use of such conventional CA inhibitors can be found e.g. in C. T. Supuran, Expert Opinion on Therapeutic Patents, 10 (5) (2000) 575-600. "Specific CA inhibitors", on the other hand, is to be understood to mean compounds which largely inhibit only one CA subtype (e.g. CA V) or a defined group of CA subtypes. The use of conventional CA inhibitors for the specific treatment and/or prophylaxis of obesity is not known.

It is generally accepted that the overwhelming majority of known cases of obesity are attributable to the comparatively excessive proportion of exogenous fats in the food intake. In highly developed countries like the USA, up to 30% of the food consumed by obese people is in the form of fats. According to current knowledge, fatty acid deposits leading to obesity accordingly originate predominantly from an excessive intake of alimentary fats. These cannot be influenced by the inhibition of DNL, which targets carbohydrate metabolism.

Thus, although a reduction in the storage of fatty acids in adipocytes is also achieved by DNL inhibition, the latter has hitherto been regarded as an unsuitable starting point for the treatment and/or prophylaxis of obesity in man because of its inherently small contribution to the storage of fatty acids in body cells. A summary of the opinions expressed by experts in this subject can be found for example in M. K. Hellerstein, European Journal of Clinical Nutrition 53 (1) (1999) 53-65. This view prevailing among experts has so far stood in the way of the specific search for drugs for the treatment and/or prophylaxis of obesity which are based on the principle of DNL inhibition, or of their development.

Within the scope of the present invention, it has now been found, surprisingly, that compounds which are capable of inhibiting DNL in mammals, especially man, can be used effectively for the treatment and/or prophylaxis of obesity, particularly if these compounds are administered to the patients in question over prolonged periods of e.g. more than six weeks. Accordingly, over prolonged periods, significant reductions in the body weight of obese persons can be achieved by DNL inhibition even though DNL per se makes only a relatively small contribution to the body fat stored in adipocytes. Thus, by means of DNL inhibition over prolonged periods, this inherently small effect can accumulate in such a way that it makes a significant overall contribution to the reduction in body weight.

Using the compound topiramate as an example, it can be shown that the method according to the invention is indeed suitable for specifically discovering compounds suitable for the treatment and/or prophylaxis of obesity. Topiramate is an antiepileptic known from EP 0 138 441 A2. Topiramate is also known to have a multifactorial pharmacological spectrum of action. Thus topiramate can block the tension-dependent sodium channels and hence stabilize the membrane potential of cells; it activates the GABA receptors and thereby enhances GABA-mediated inhibition; it acts as a carboanhydrase inhibitor, and it is capable of inhibiting the AMPA/kainate receptors, a subtype of the glutamate receptors, thereby inhibiting the appearance of AMPA-induced flows. Accordingly, topiramate exhibits pronounced effects on the CNS. It is not known whether the antiepileptic properties of topiramate are attributable to the pharmacologically relevant factors mentioned above.

It is known from WO 98/00130 that topiramate also possesses pharmacological properties which make it appear suitable for the treatment of obesity. These properties were discovered by chance as side effects in long-term studies on epileptic patients. It is not yet known which pharmacological properties of topiramate are responsible for the weight loss observed in epileptic patients. Topiramate is one of a group of anticonvulsant compounds of a general formula I indicated in WO 98/00130 as suitable for the treatment of obesity.

By the method according to the invention, it was now possible to show that topiramate is a potent CA inhibitor, especially a potent inhibitor of carboanhydrases of subtypes II and V occurring in mammals, and that topiramate is capable of effectively inhibiting DNL in mammalian cells. Thus the method according to the invention made it possible for the first time to prove that the hitherto inexplicable pharmacological side effects of topiramate leading to weight loss in epileptic patients are based substantially on its ability effectively to inhibit DNL in mammals. It is accordingly to be expected that the method according to the invention will make it possible in the future to discover compounds suitable for the treatment and/or prophylaxis of obesity. The method according to the invention thus opens up for the first time the possibility of discovering, with comparative speed and ease, pharmacologically potent compounds which act according to the principle of DNL inhibition. By virtue of the present invention, compounds acting according to the above-mentioned principle and suitable for the treatment and/or prophylaxis of obesity can now be selected, at least in a first preliminary selection process, without lengthy and expensive in vivo tests such as test-animal feeding experiments.

These results are surprising as earlier investigations into the pharmacological properties of topiramate indicated that its CA-inhibitory activity was always unexceptional or even rather small and of no therapeutic importance (cf. e.g. B. E. Maryanoff et al., Journal of Medicinal Chemistry 30 (1987) 880-887; B. E. Maryanoff et al., Journal of Medicinal Chemistry 41 (1998) 1315-1343; S. J. Dodgson et al., Epilepsia 41 (1) (2000) p. 35-p. 39). In the earlier investigations mentioned above, the CA-inhibitory activity of topiramate was always determined using test solutions containing CA from different mammals, which still contained various body constituents such as blood or organ tissue.

In a first embodiment of the method according to the invention, compounds suitable for the treatment and/or prophylaxis of obesity can be discovered by selecting as suitable those compounds which are capable of inhibiting the activity of at least one carboanhydrase occurring in mammals. For example, at least one test compound can be brought into contact with at least one carboanhydrase and those compounds which inhibit the activity of at least one carboanhydrase can then be identified in a manner known per se. In this embodiment it is preferable to use carboanhydrases which occur in mammals such as man or rodents, for example rats, mice or guinea-pigs, especially carboanhydrases of subtypes II and/or V. It is particularly preferable to use carboanhydrases which occur in man. For example, suitable carboanhydrases can be isolated from the above-mentioned mammals and purified if desired, or they can preferably be prepared by chemical or biotechnological methods known per se.

In a preferred variant of this first embodiment, the change in activity of the carboanhydrases under the influence of the test compounds can be determined in an in vitro enzyme activity test known per se, the carboanhydrases being present as isolated enzymes which have been at least substantially freed of impurities. It is preferable to use carboanhydrases which have been prepared by chemical or biotechnological methods as these can be used in especially pure form. In vitro activity tests for determining the activity of carboanhydrases are known per se. The in vitro enzyme activity tests which are suitable within the scope of the present invention to determine changes in the activity of carboanhydrases and include, for example, the measurement of the change in pH value under the influence of carboanhydrases, (cf. K. M. Wilbur, N. G. Andersen, Journal of Biological Chemistry 176 (1948) 147-154; G. Sanyal, T. H. Maren, Journal of Biological Chemistry 256 (1981) 608-612), the stop-flow-measurement method (cf. R. G. Khalifah, Journal of Biological Chemistry 246 (1971) 2561-2573) or the 4-nitrophenylacetate-esterase method (cf. Y. Pocker, J. T. Stone, Journal of the American Chemical Society 87 (1965) 5497-5498). In the latter test, the rate of hydrolysis of 4-nitrophenylacetate under the influence of the carboanhydrases to be investigated is determined, in which the property of carboanhydrases also to act as esterases is utilized.

According to the invention, a test method for determination of the CA-inhibitory properties of compounds which is described by C. T. Supuran et al., European Journal of Medicinal Chemistry 33 (1998) 577-594 (cf. p. 592 in particular; cited hereafter as "Supuran et al.") or by A. Scozzafava et al., Journal of Medicinal Chemistry 42 (1999) 3690-3700 (cf. p. 3697 in particular; cited hereafter as "Scozzafava et al.") is preferentially suitable in this context.

Within the scope of the disclosure of the present invention, express reference is hereby made to these test methods described by Supuran et al. and Scozzafava et al. Compounds which have $IC_{50}$ values of at least 10 µmol/liter or below (=higher activity) in one of the above-mentioned in vitro standard activity tests according to Supuran et al. or Scozzafava et al. can be selected as suitable CA-inhibitory compounds (=CA inhibitors) in terms of the present invention. If the activity of human CA subtypes is to be determined, methods other than the 4-nitrophenylacetate-esterase method may be better suited. In particular, methods which make it possible also to have relatively rapid reactions may be suitable.

In an enzyme activity test (originally described by Y. Pocker and J. T. Stone, Biochemistry 6 (1967) 668-678) operating according to the 4-nitrophenylacetate-esterase method described by Scozzafava et al. (vide supra) in terms of the present invention it was demonstrated that topiramate has a pronounced inhibitory action on human carboanhydrase of subtype II ($IC_{50}$=5 nmol/liter) obtained by biotechnological methods, and that this inhibitory action is considerably stronger than the inhibitory action caused by the conventional CA inhibitors acetazolamide or methazolamide measured as reference substances. The human carboanhydrase of subtype II was obtained by the method described by Scozzafava et al.

In the same test, it was demonstrated that topiramate also has a pronounced inhibitory action on carboanhydrase of the subtype Va of mice (=mCA Va) which is obtained by biotechnological processes ($IC_{50}$=74 nmol/l). In a departure from the test procedure described by Scozzafava et al, in this case the enzyme mCA Va was used in a concentration of 120 nM. The mCA Va was obtained in known manner by the method described by H. R. Heck et al., Journal of Biological Chemistry 269 (1994) 24742-24746. To this end, the strain of bacteria *Escherichia coli* BL 21 (DE3) was used, which was used with a plasmid vector which contained the sequence coding for mCA Va under the control of the T7 promoter which can be induced by isopropyl-β-D-thiogalactopyranoside (IPTG). The bacterial culture was inoculated at 37° C. with stirring into a Luria-Bertani liquid medium containing ampicillin (100 µg/ml) and its growth was monitored by spectrophotometry at 600 nm. Once the bacterial culture had entered the exponential growth phase, IPTG was added in a final concentration of 1 mmol/liter. After 3 hours incubation time (37° C. with stirring), the bacterial culture was centrifuged at 7000×g for 15 minutes, and the supernatant was discarded. The resulting pellet was taken up in 0.1 vol twice-distilled water, and lysozyme (100 µg/ml) was added thereto. The cell lysis took place under ultrasound treatment. To this end, 10 ml aliquots of the resulting bacterial suspension were poured into a glass vessel which was open at the top, and each of these samples was treated with ultrasound 4 times for 3 minutes. After each ultrasound pulse, the absorption of the samples was determined at 600 nm, for which each 100 µl of a-sample was diluted with 900 µl twice-distilled water. The end point was reached once the value of the 600 nm absorption of a sample was about 1/10 of the initial value. Once cell lysis had taken place, $CaCl_2$-binding buffer (Stratagene) was added, and the resulting cell lysate was poured on to a calmodulin Affinity resin column for purification. The purification is based on the high affinity of the calmodulin domain which is bound to the resin to the calmodulin binding peptide tag which is present at the N-terminal end of the expressed mCA Va protein. The purification was effected in known manner (cf. manual "Affinity LIC Cloning and Protein Purification Kit Manual" from Stratagene).

In a second embodiment of the method according to the invention, compounds suitable for the treatment and/or prophylaxis of obesity can be discovered by selecting those compounds which are capable of reducing the amount of metabolic products formed in the citric acid cycle of isolated living mammalian cells or of lipidic secondary products of the citric acid cycle. Suitable metabolic products of the citric acid cycle whose amount is measurably reduced under the influence of the test compounds include acid-soluble metabolic products such as citrate, maleate, fumarate and/or α-ketoglutarate. Citrate is preferred. Furthermore, lipidic secondary products of the citric acid cycle, such as free fatty acids, are suitable as metabolic products. Lastly, in this second embodiment, the ability of the test compounds to inhibit the activity of at least one carboanhydrase occurring in mammals is also determined, although the test model used is set up differently from the first embodiment mentioned. The process of the second embodiment is based on the principle of determining in known manner the uptake of radioactivity from substrates of the citric acid cycle labeled with the $^{14}C$-isotope into metabolic intermediate products or secondary products of the citric acid cycle of isolated, living mammalian cells and comparing the results obtained with the results obtained under otherwise identical conditions, but under the influence of CA-inhibitory compounds. Isolated living cells of rodents such as rats, mice or guinea-pigs, or of man, are preferably used in this variant of the method. Human cells are preferred. If cells of rodents are used, these can be adipocytes or hepatocytes. Adipocytes of rodents are preferred. If human cells are used, adipocytes or hepatocytes may be used. Human hepatocytes are preferred. The mammalian cells used in this variant of the method can be obtained by conventional culture and/or cloning processes. Natural or biotechnologically modified mammalian cells can be used. If the uptake of radioactivity in acid-soluble intermediate products of the citrate cycle is to be determined, preferably $^{14}C$-hydrogen carbonate (=NaH[$^{14}C$]$O_3$) is used as the $^{14}C$-labelled substrate. If the uptake of radioactivity in lipidic secondary products of the citrate cycle is to be determined, preferably [U-$^{14}C$]glucose is used as the $^{14}C$-labelled substrate.

A preferred variant of this second embodiment for determining the ability of compounds to inhibit DNL in mammals is indicated by S. A. Hazen et al. in FASEB Journal 10 (4) (1996) 481-490 (cited hereafter as "Hazen et al."). Within the scope of the disclosure of the present invention, express reference is hereby made to this test method described by Hazen et al. Compounds which, in this test according to Hazen et al., significantly inhibit the incorporation of radioactivity from $^{14}C$-labelled substances which can serve as precursors in the citric acid cycle, for example the incorporation of $^{14}C$-bicarbonate into citrate, maleate, fumarate and/or α-ketoglutarate, with an $IC_{50}$ value of at least 10 µmol/l or below (=higher activity) can be selected as suitable compounds in terms of the present invention.

In a test model corresponding to that described by Hazen et al., which was carried out within the scope of the present invention, topiramate exhibited a pronounced inhibitory effect on the formation of acid-soluble metabolic products of the citric acid cycle of rat adipocytes of the 3T3-F442A cell line obtained by biotechnological methods. This inhibitory effect of topiramate ($IC_{50}$=348 nmol/liter) was markedly more pronounced than the effect of the conventional CA inhibitor ethoxzolamide measured as a reference substance.

In a particularly preferred variant of the method according to the invention for discovering compounds suitable for the treatment and/or prophylaxis of obesity, those compounds are selected which, in the above-mentioned first embodiment of the method, especially in an above-mentioned in vitro enzyme activity test, have been selected as suitable for inhibiting at least one carboanhydrase occurring in mammals, and which additionally, in the above-mentioned second embodiment of the method, have been selected as suitable for reducing the amount of metabolic products formed in the citric acid cycle of isolated living mammalian cells as well. In the first embodiment of the method, the ability of compounds to inhibit carboanhydrases occurring in mammals can be checked rapidly and effectively. The second embodiment of the method provides, inter alia, clues as to whether the compounds investigated are also capable of penetrating mitochondria of living mammalian cells where CA V is located. Suitable compounds can be selected by carrying out the first and second above-mentioned embodiments in parallel or successively in either order.

According to the invention, compounds which are capable of inhibiting DNL in mammals are suitable for the preparation of drugs for the treatment and/or prophylaxis of obesity. Compounds selected here are those which are capable of inhibiting at least one carboanhydrase occurring in mammals. The selected compounds must of course be physiologically compatible and meet the demands generally made on pharmaceutical active substances, e.g. regarding safety and compatibility. It is preferable to use compounds which are capable of inhibiting carboanhydrases of subtypes II and/or V occurring in mammals. Particularly preferred compounds are those which are capable specifically of inhibiting CA II and/or CA V, especially CA V.

Previously known compounds with a CA-inhibitory effect which cause a reduction in patients' body weight after prolonged administration, for example topiramate, also have pronounced effects directed towards the CNS, for instance anticonvulsant effects. Side effects directed towards the CNS are often undesirable for compounds which are intended for long-term administration aimed at the treatment and/or prophylaxis of obesity. Compounds which have been selected by the above-mentioned method according to the invention as suitable for the treatment and/or prophylaxis of obesity can therefore additionally be tested for effects directed towards the CNS. For example; the compounds can be tested for any anticonvulsant properties which may be present. An example of a suitable method of testing compounds for anticonvulsant properties is the so-called "supramaximal electroshock test" (=SES test, occasionally also referred to as the "maximal electroshock test" or MES test) according to G. Chen et al., Proceedings of the Society for Experimental Biology and Medicine 87 (1954) 334-339 (cited hereafter as "Chen et al.") and J. E. P. Toman et al., Journal of Neurophysiology 9 (1946) 231 (cited hereafter as "Toman et al."). Within the scope of the disclosure of the present invention, express reference is hereby made to this test method described by Chen et al. and Toman et al. Thus compounds which are aimed at the treatment and/or prophylaxis of obesity by administration to patients over prolonged periods should be substantially ineffective in the above-mentioned SES test according to Chen et al. and Toman et al., and should preferably have no effects to be regarded as significant according to the criteria conventionally applied to this test, even in higher doses of at least 100 mg/kg p.o. (i.e. protective dose, $PD_{50}$, according to G. Chen et al. $\geqq 100$ mg/kg p.o.; the $PD_{50}$ values given by G. Chen et al. substantially correspond here to the more common indication of dose as the minimum effective dose, MED). Compounds which have been selected as suitable in the above-mentioned method of discovering compounds, and which additionally are substantially ineffective in the above-mentioned MES test according to Chen et al., are particularly suitable for the preparation of pharmaceutical compositions for the treatment and/or prophylaxis of obesity. The SES (or MES) tests are standard pharmacological tests and can be performed as routine methods by appropriate service providers (e.g. "Panlabs").

The compounds identified by the method according to the invention as being suitable for the treatment and/or prophylaxis of obesity can usually be contained as drugs with conventional pharmaceutical auxiliary substances in galenic formulations, e.g. tablets, capsules, suppositories or solutions. These galenic formulations can be prepared by methods known per se using conventional solid or liquid excipients, e.g. lactose, starch or talcum or liquid paraffins, and/or using conventional pharmaceutical auxiliary substances, for example tablet disintegrants, solubilizers or preservatives. Pharmaceutical preparations suitable according to the invention are for example also known from EP 0 138 441 A2 and from WO 98/00130.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A method of preparing a pharmaceutical composition for treating or inhibiting obesity, said method comprising:
   identifying a compound which inhibits de novo lipogenesis in a mammal, wherein said compound is identified as a compound which inhibits de novo lipogenesis by measuring inhibitory activity of at least one candidate compound on carboanhydrase activity of at least one mammalian carboanhydrase,
   selecting said candidate compound as a compound which inhibits de novo lipogenesis if said candidate compound exhibits inhibition of carboanhydrase activity of at least one mammalian carboanhydrase, and
   incorporating the selected compound which inhibits de novo lipogenesis with at least one conventional solid or liquid excipient or at least one conventional pharmaceutical auxiliary substance in a pharmaceutical composition for treating or inhibiting obesity.

2. The method according to claim 1, wherein said at least one mammalian carboanhydrase comprises a mammalian carboanhydrase of subtype II or subtype V.

* * * * *